US010265432B2

(12) United States Patent
Paranhos et al.

(10) Patent No.: US 10,265,432 B2
(45) Date of Patent: Apr. 23, 2019

(54) EQUIPMENT FOR SANITIZING THE AIR CONDITIONING SYSTEM OF VEHICLES BY MEANS OF RADIANT CATALYTIC IONIZATION

(71) Applicant: DBG Group Investments, LLC, Dallas, TX (US)

(72) Inventors: Frederico Monteiro Paranhos, Sao Paulo (BR); Joao da Costa Pilao Neto, Sao Paulo (BR); Andrew Eide, Rockwall, TX (US)

(73) Assignee: DBG GROUP INVESTMENTS, LLC, Dallas, TX (US)

( * ) Notice: Subject to any disclaimer, the term of this patent is extended or adjusted under 35 U.S.C. 154(b) by 218 days.

(21) Appl. No.: 15/470,466

(22) Filed: Mar. 27, 2017

(65) Prior Publication Data

US 2017/0197493 A1 Jul. 13, 2017

Related U.S. Application Data

(63) Continuation-in-part of application No. 14/900,605, filed as application No. PCT/IB2014/001557 on Jun.
(Continued)

(30) Foreign Application Priority Data

Jan. 17, 2012 (BR) .......................... 1020120011220
Jun. 19, 2013 (BR) .......................... 1320130154163

(51) Int. Cl.
*A61L 9/22* (2006.01)
*A61L 2/10* (2006.01)
(Continued)

(52) U.S. Cl.
CPC ................. *A61L 9/205* (2013.01); *A61L 2/10* (2013.01); *A61L 2/14* (2013.01); *A61L 9/22* (2013.01);
(Continued)

(58) Field of Classification Search
CPC ... A61L 9/20; A61L 9/22; A61L 9/205; A61L 2/10
See application file for complete search history.

(56) References Cited

U.S. PATENT DOCUMENTS 6,773,682 B1 8/2004 Benda
9,603,961 B2 3/2017 Paranhos
(Continued)

FOREIGN PATENT DOCUMENTS

BR 9306305 A 6/1998
EP 1450870 A 5/2006
(Continued)

OTHER PUBLICATIONS

International Search Report and Written Opinion issued in PCT/IB2014/001557 dated Dec. 24, 2014.
(Continued)

*Primary Examiner* — Sean E Conley
(74) *Attorney, Agent, or Firm* — Workman Nydegger (57) ABSTRACT

An air sanitization device is provided that utilizes radiant catalytic ionization to produce purifying plasma comprising highly oxidative molecules that greatly decrease the amount of volatile organic compounds, carbon monoxide and particulate matter within the HVAC system and the interior of transportation vehicle. The air sanitation device includes surfaces coated or impregnated with a noble alloy that comprises predominately titanium dioxide and a UV light source that directs UV light onto the surfaces of coated surfaces to generate, via the radiant catalytic ionization
(Continued)

reaction the purifying plasma. Integration of the air sanitization device into a vehicle HVAC system greatly decreases irritant molecules within the vehicle.

20 Claims, 5 Drawing Sheets

Related U.S. Application Data 19, 2014, now Pat. No. 9,603,961, application No. 15/470,466, which is a continuation-in-part of application No. 14/372,637, filed as application No. PCT/BR2013/000020 on Jan. 17, 2013, now Pat. No. 9,937,276.

(51) Int. Cl.
  A61L 9/20 (2006.01)
  A61L 2/14 (2006.01)
  B60H 3/00 (2006.01)
  B60H 3/06 (2006.01)

(52) U.S. Cl.
  CPC ........ B60H 3/0078 (2013.01); A61L 2202/14 (2013.01); A61L 2209/111 (2013.01); A61L 2209/12 (2013.01); A61L 2209/14 (2013.01); A61L 2209/16 (2013.01); A61L 2209/211 (2013.01); B60H 2003/0675 (2013.01)

(56) References Cited

U.S. PATENT DOCUMENTS

| | | |
|---|---|---|
| 9,937,276 B2 | 4/2018 | Neto |
| 2004/0251122 A1 | 12/2004 | Goswami |
| 2005/0063881 A1 | 3/2005 | Senne et al. |
| 2005/0169821 A1 | 8/2005 | Boschert et al. |
| 2006/0127288 A1 | 6/2006 | Hay et al. |
| 2009/0035176 A1 | 2/2009 | Normark et al. |
| 2009/0117001 A1 | 5/2009 | Hyde et al. |
| 2010/0126190 A1 | 5/2010 | Ha |
| 2010/0266445 A1 | 10/2010 | Campagna |
| 2012/0093691 A1 | 4/2012 | Mole |
| 2014/0363342 A1 | 12/2014 | Neto |

FOREIGN PATENT DOCUMENTS

| | | |
|---|---|---|
| GB | 1202065 A | 8/1970 |
| WO | 2012081086 A1 | 6/2012 |

OTHER PUBLICATIONS

Office Action issued in U.S. Appl. No. 14/900,605 dated Mar. 24, 2016.
Notice of Allownce issued in U.S. Appl. No. 14/372,637 dated Nov. 16, 2017.
Office Action issued in U.S. Appl. No. 14/372,637 dated Feb. 28, 2017.
Office Action issued in U.S. Appl. No. 14/372,637 dated Sep. 21, 2016.
Office Action issued in U.S. Appl. No. 14/372,637 dated Feb. 2, 2016.
Notice of Allowance issued in U.S. Appl. No. 14/900,605 dated Jan. 6, 2017.
Notice of Allowance issued in U.S. Appl. No. 14/900,605 dated Dec. 21, 2016.
Patent Cooperation Treaty: International Search Report for PCT/BR2013/000020; Torres, Jose Antonio Guzman; dated May 4, 2013; 6 pages (including BR translation).

EQUIPMENT FOR SANITIZING THE AIR CONDITIONING SYSTEM OF VEHICLES BY MEANS OF RADIANT CATALYTIC IONIZATION

CROSS-REFERENCE TO RELATED APPLICATIONS

This application is a continuation-in-part application of U.S. patent application Ser. No. 14/900,605, filed on Dec. 21, 2015, entitled EQUIPMENT FOR SANITIZING THE AIR CONDITIONING SYSTEM OF VEHICLES BY MEANS OF RADIANT CATALYTIC IONIZATION, which is a National Stage Entry of International Application Ser. No. PCT/IB2014/001557, filed on Jun. 19, 2014, entitled EQUIPMENT FOR SANITIZING THE AIR CONDITIONING SYSTEM OF VEHICLES BY MEANS OF RADIANT CATALYTIC IONIZATION, which claims priority from Brazil Patent Application No. 1320130154163, filed on Jun. 19, 2013, which is a Certificate of Addition of and claims priority from and/or benefit of Brazil Patent Application No. 1020120011220, filed 17 Jan. 2012, each of which is incorporated herein by reference in their entirety; and this application is also a continuation-in-part of U.S. patent application Ser. No. 14/372,637, filed on Jul. 16, 2014, entitled DEVICE FOR SANITIZING THE AIR-CONDITIONING SYSTEM OF VEHICLES USING RADIANT CATALYTIC IONIZATION, which is a National Stage Entry of International Application Ser. No. PCT/BR2013/000020), filed Jan. 17, 2013, which claims priority from Brazil Patent Application No. 1020120011220, filed Jan. 17, 2012, and entitled EQUIPAMENTO PARA HIGIENIZAçÃO DO SISTEMA DE AR CONDICIONADO DE VEÍCULOS POR MEIO DE IONIZAçÃO RADIANTE CATALÍTICA, each of which is incorporated herein by reference in their entirety.

TECHNICAL FIELD

This invention relates to equipment for sanitizing the air conditioning system of vehicles by means of radiant catalytic ionization, in particular, to sanitizing equipment that uses the radiant catalytic ionization technology, promoting a reaction between UVX light and a noble metal alloy generating a purifying plasma, efficient in sanitizing not only the air conditioning, but also the interior environment of vehicles. Additionally, this application relates to equipment for sanitizing the air conditioning system and interior of vehicles in general through the transformation of the ambient air into a purifying plasma primarily containing hydrogen peroxide and hydroxyl radicals.

Embodiments may also include sanitizing equipment that have a field of application in the automotive sector, notably in air conditioning and the interior environment of transportation vehicles in general. Additionally, embodiments may also have a field of application in the heating, ventilation and air conditioning (HVAC) systems or equipment for sanitizing the HVAC system and the interior of vehicles in general through the transformation of ambient air into purifying plasma primarily containing hydrogen peroxide and hydroxyl radicals. Moreover , embodiments can also be applied or incorporated into the HVAC system of various transportation vehicles, including but not limited to, land, sea, or air vehicles such as, for example, trains, busses, rail vehicles, boats, submarines, airplanes, trams, or other personal or public transportation vehicles (hereinafter referred to as "vehicles" or "transportation vehicles."

BACKGROUND

The existing solutions for sanitizing interiors and air conditioning systems of, for example, automotive vehicles are based on technologies that use various resources, among these the application of chemical products and manual mechanical intervention, vaporization/nebulization system for chemical products, oxi-sanitizing of interiors, which consists of applying ozone, among others.

Among the conventional practices used to sanitize interiors and air conditioning systems, some drawbacks stand out that deserve mention, for example:

Application of chemical products and manual mechanical intervention:
  This method needs technically skilled labor, which increases the application cost;
  Mechanical intervention does not reach all possible contaminated spots due to its physical limitations, and takes more time for its execution;
  Chemical products (those that do not comply with regulatory standards) when applied can cause general discomfort to users due to possible human allergic sensitivity.
Vaporization/nebulization system for chemical products:
  A deficiency of vaporization/nebulization systems is their known limitations for being able to reliably resolve and not just cover up sanitizing and odor problems, which compromises their efficiency and effectiveness;
Thus, this system also compromises the final quality of the services rendered.
Oxi-sanitizing of interiors:
  A deficiency of this technique is the risk that the application of ozone in interior environments can in a general way harm the health of users;
  In improperly measured amounts, ozone concentration in interior environments can cause respiratory discomforts, nausea, and mucous membrane oxidation, among other unwanted reactions or irritations to humans.

In the face of this situation and the deficiencies inherent in current sanitizing practices, there is a need to develop equipment capable of accomplishing in the internal environment of a vehicle significant, reliable removal of odors human irritants without the use of chemical agents. The focus of this application is to provide a device and method to help resolve the deficiencies of prior sanitizing practices.

The prior art includes some patent documents that deal with the matter in question. For example, Brazilian Patent No. PI9306305-9, titled "PROCESS AND SYSTEM FOR AIR DISINFECTION IN AIR CONDITIONING DUCTS," is directed to a process for disinfecting air that consists of aerosol type vaporization of a deodorant that includes a quaternary ammonia compound, more specifically benzyl ammonium chloride, which is nonpoisonous and substantially nonvolatile. The benzyl ammonium chloride is mixed in water which by means of micro vaporizers goes through and is provided via the air flow in a duct.

The above solution, although appealing in order to disinfect air in air conditioning or HVAC system ducts, has a limitation factor in the matter of aerosol vaporization, which will certainly not go through the whole pipe, making its application ineffective, and also it utilizes ammonia as a disinfectant, which, although not poisonous, may not be tolerated by some organisms including humans, resulting in adverse allergic reactions.

SUMMARY

Cognizant of the prior existing solutions, including its gaps and limitations, studies and research were performed in order to develop embodiments of equipment for sanitizing the HVAC systems of vehicles by means of radiant catalytic ionization, which in general is sanitizing equipment that uses radiant catalytic ionization technology that promotes a reaction between ultraviolet or UVX light and a noble metal alloy so as to generate a purifying plasma comprised mainly of hydrogen peroxide, which is efficient in sanitizing the HVAC systems as well as the interior of transportation vehicles.

In short, invention embodiments may have one or more of the following advantages, each of which may improve the efficiency and effectiveness in sanitizing the interior, the air conditioning system, and/or HVAC systems of transportation vehicles. As such embodiments may have attributes that enable:

An embodiment to remove odors of most possible origins;
An embodiment to not need skilled labor for its application;
An embodiment to be directly applied or installed in the environment in the presence of people, without needing to isolate the site for any period of time;
An embodiment to be incorporated into equipment that is easy to handle and operate;
An embodiment having an active principle that includes hydrogen peroxide, which is an oxidant present in nature and therefore does not require any manufactured chemical products;
An embodiment that during operation emits odorless and neutral smelling characteristics as perceived by a user or vehicle occupant;
An embodiment that does not use chemical products, thereby reducing the incidence of possible side effects due to the use of unregulated products, even when applied in inadequate amounts;
An embodiment that does not require mechanical intervention for application or removal, because such embodiments may use only air as the dissemination or carrier medium;
An embodiment that does not use ozone, which, though also using air as the conducting or carrier medium, can cause health problems, in contrast to the technology utilized in various embodiments.

In some embodiments of the invention a device is provided that has a first and a second module. The first module comprises a UVX lamp configured to produce UV light. The first module also has a first and a second honeycomb structure of surfaces. Each honeycomb structure is impregnated or coated with a noble metal allow and configured to generate via a radiant catalytic ionization reaction with the UV light, a purifying plasma comprising oxidative sanitizing molecules. The first and the second honeycomb structures are each positioned in locations that are adjacent to the UVX lamp such that the UV light can impinge on a majority of the surfaces making up the honeycomb structures while air flows thereover. The first module may also include a first frame on which the UVX lamp and the first and the second honeycomb structure of surfaces are mounted. Additionally, the first module may include a cover portion the combines or attaches to the first frame to establish an enclosure that enables air to pass through the first and the second honeycomb structure of surfaces when the first module is positioned in a duct of a HVAC system of a transportation vehicle.

In some embodiments, the second module may be located remotely from the first module. The second module is electrically connected to the first module by one or more electrical connections. The second module comprises control circuitry that includes components to provide power and control functions of the UVX lamp and that connect to the transportation vehicle's control circuitry. The second module may be configured to be positioned within or proximate to a control console of the transportation vehicle while being remote from the first module.

In some embodiments the first module may also include a fan for pushing or pulling air flow over the surfaces of the first and the second honeycomb structure of surfaces.

In other embodiments, the first cover portion is integral with the duct of the HVAC system.

In some embodiments, the UVX lamp comprises a plurality of UVX LEDs.

In various embodiments, the purifying plasma comprises hydrogen peroxide and hydroxyl radicals. The purifying plasma uses air as a carrier medium.

In yet other embodiments, the duct of the HVAC system is an output duct that passes HVAC system treated air into a passenger compartment of the transportation vehicle.

In some embodiments, the first cover portion combines with the first frame to establish an exterior covering about the first module with openings that enable air to pass through the first and the second honeycomb structure of surfaces.

Additionally in some embodiments, a temperature sensor is positioned in the first module and configured to sense an output temperature of the purifying plasma from the first module, wherein the control circuitry is configured to turn off the UVX lamp if the sensed output temperature is greater than a predetermined temperature when the HVAC system of the transportation vehicle is set to cool the interior air of the transportation vehicle to a user set temperature as a maximum rate.

Also in some embodiments, an airflow sensor is positioned in the first module to sense a flow of air or plasma through the first module, wherein the control circuitry is configured to turn off the UVX lamp if the sensed output of the air flow sensor indicates that the flow of air or plasma is below a predetermined flow rate.

In another embodiment of the invention a transportation vehicle is provided that comprises an HVAC system that is integrated into the transportation vehicle. The HVAC system includes an air duct configured to distribute HVAC system conditioned air into the interior of the transportation vehicle, such as an automobile. The transportation vehicle also includes an air sanitizing device integrated into the HVAC system; the air sanitizing device may comprise a first module. The first module of the air sanitizing device comprises a UVX lamp configured to produce UV light. The first module may also include a first and a second air permeable structure, such as a honeycomb, mesh, woven, screen, louvres, slotted or other structure having a plurality of surfaces, wherein each air permeable structure has surfaces is impregnated or coated with a noble metal alloy, such as titanium dioxide, and configured to generate, via a radiant catalytic ionization reaction with the UV light, a purifying plasma comprising oxidative sanitizing molecules; the first and second air permeable structures each are positioned adjacent to the UVX lamp such that the UV light can impinge on a majority of the air permeable structure's surfaces while air flows thereabout and there over. The first module may also include a first frame on which the UVX lamp and the first and second air permeable structures having a plurality of surfaces are mounted. The first frame is configured to be positioned in the air duct such that air is enabled to pass through, and in some embodiments about, the first and second air permeable structure's surfaces. The air sanitizing device also comprises a second module positioned or located in the vehicle, yet remotely from the first module. The second module is connected to the first module by an electrical connection of one or more conductive connections the may carry power or signals between the first and second modules. The second module comprises control circuitry that includes components and circuitry that provide power to the first module and control functions associated with the UVX lamp or other devices or sensors that are part of the first module, such as temp sensors or a fan. The second module is configured to be positioned within or proximate to a control console of the transportation vehicle while being remote from the first module. The second module may connect via a second electrical connection to a vehicle control circuit.

In some embodiments, the first module further comprises a first cover portion that combines with or removably attaches to the first frame to establish an enclosure that enables passage of air through the first and the second honeycomb structure surfaces. The first cover portion may be integral with the air duct of the HVAC system. In other embodiments the first cover portion my comprise the air duct of the HVAC system to which the frame of the first module is mounted.

In another embodiment of the invention air sanitizing device is provided. The air sanitizing device is configured to be integrated with an HVAC system. The air sanitizing device comprises a first module and a second module. The first module comprises a UVX lamp configured to produce UV light. The first module also comprises at least a first air permeable structure having a plurality of surfaces, each air permeable structure having at least a portion of its surfaces impregnated or coated with a noble metal alloy, which includes titanium dioxide, and configured to generate, via a radiant catalytic ionization reaction with the UV light, a purifying plasma comprising oxidative sanitizing molecules; the at least first air permeable structure having surfaces each being positioned adjacent to the UVX lamp such that the light can impinge on a majority of the surfaces while air flows there over or thereabout. The first module may also include a first frame on which the UVX lamp and the at least one air permeable structure of surfaces are mounted. The first frame is configured to be positioned in the air duct such that air within the air duct is enabled to pass through and over the surfaces of the air permeable structure and it surfaces. The second module of the air sanitizing device is located remotely from the first module. The second module is connected to the first module by an electrical connection that may carry power or signals between the two modules. The second module comprises control circuitry that includes component circuitry configured to provide power and control functions for the UVX lamp and, in some embodiments, logic and connection circuits for integration with the HVAC system of the transportation vehicle control circuitry. The second module may be configured to be positioned within, proximate to, or remotely from a control console and/or control circuitry of the transportation vehicle while being remote from the first module. The second module may be connected to the vehicle control circuitry by an electrical cable or connections.

BRIEF DESCRIPTION OF THE DRAWINGS

For a more complete understanding, reference is now made to the following detailed description taken in conjunction with the accompanying illustrative Drawings in which.

DETAILED DESCRIPTION

Referring now to the drawings, wherein like reference numbers are used herein to designate like elements throughout, the various views and embodiments of the equipment for sanitizing the air conditioning system of vehicles by means of radiant catalytic ionization are illustrated and described. In addition, other possible embodiments are also described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring to FIGS. 1-4, the equipment for sanitizing the air conditioning system of vehicles by means of radiant catalytic ionization, relates to equipment 10 mounted in a framework 20 that is able to hold a UVX light bulb 30 surrounded at least on two sides by a beehive or honeycomb structure 40 that is impregnated or coated with a metal alloy so that the honey comb structure 40 transforms air/oxygen (A) into a purifying plasma (P) composed of hydroxyl radicals and hydrogen peroxide.

More particularly, embodiments of the sanitizing equipment 10 comprise a framework 20 with symmetrical and opposing circular cavities or openings where there is intake 50 for accepting surrounding air (A) to be drawn by a fan 60 into the equipment 10. The intake fan 60 is equipped with a protective grating 70 between the fan 60 and the exterior of the sanitizing equipment. There is an outlet cavity or opening 75 allowing passage of purifying plasma (P), through an insufflation grating 80, for passage out of the equipment 10 and into the surrounding air (A). Properly speaking, the air (A) inters through the intake 50 and passes by a UVX light bulb 30 located in the intermediate internal part 45 of the framework's interior. In this way, UVX light bulb 30 is surrounded by a beehive or honeycomb structure 40 having surfaces that are impregnated or coated with a noble metal alloy, which predominantly comprises titanium dioxide. In this context, upon switching on the connect-disconnect switch (ON-OFF switch) 90, the UVX light bulb 30 is lighted and the fan 60 pulls or pushes air through the framework's interior, thus processing and transformation air into an air purifying plasma (P) comprised of hydroxyl radicals and hydrogen peroxide. The air purifying plasma (P) could be applied at two different ventilation or fan speeds as controlled by speed button 100, as well as having an application time predetermined by a digital timer relay with hour, minutes and seconds activated by operational control 110. The equipment is supplemented by a number of applications counter 120 and cell or control unit 130, which comprises circuitry responsible for the operation of the UVX light bulb unit 30.

Embodiments of the invention utilize radiant catalytic ionization technology, which, through a reaction between UVX light, a noble metal alloy and air, produces purifying plasma composed mainly of hydrogen peroxide, and may also comprise hydroxyl radicals and various other components. When air passes through a honeycomb structure 40 that has its surfaces impregnated or coated with a noble metal alloy, including titanium dioxide, while a UVX lamp 30 proximate to the honeycomb structure 40 emits UVX light that impinges on surfaces of the honeycomb structure(s) 40. Thus, generation of the plasma (P) is achieved through radiant catalytic ionization. Furthermore, the purifying plasma uses air as it carrier medium.

The air (A) is drawn in into the sanitizing equipment 10 through an intake 50 by means of a fan 60. In some embodiments a protective grating 70 is positioned over the intake area and adjacent to the fan 60, such that the intake air flows through the protective grating 70 as it enters the interior of the framework 20. The fan 60 may be activated before, after or simultaneously when the UVX lamp is turned on via the ON-Off switch 90.

A cell or control unit 130 contains circuitry that controls the workings of the UVX bulb 30, the fan 60, and other electronics that control and track the workings of the sanitizing equipment 10. In some embodiments, the control unit 130 is detachably attached to the framework 20 with an electrical connection 132 there between. The control circuitry within the control unit is connected via the electrical connection 132 to control the ON-OFF and intensity of the UVX bulb 30, the speed of the fan 50 in accordance with how a user set up the operational control 110 of the equipment 10. In various embodiments, the control circuitry of the control unit 130 also monitors one or more sensors 136 mounted within the framework. The one or more sensors may monitor temperature or humidity in order to provide feedback to the control circuitry in order to 1) increase or decrease the UV intensity output of the UVX bulb depending on whether the humidity is above or below a predetermined humidity range, or 2) increase the fan speed if the temperature within the equipment is above a predetermined range in order to cool the UVX bulb.

In some embodiments the UV light is produced by a plurality of UVX LEDs positioned to emit UV light onto the surfaces of the honeycomb structure(s) 40. A honeycomb structure is used to maximize the surface area of the noble metal alloy coating that UV light can impinge on inside the limited area of the framework interior proximate to the UVX bulb or LEDs.

In other embodiments, the ON-OFF switch 90, speed button 100, operational control 110 and number of operations counter may be positioned on the detachable control unit 130 so that the control unit 130 can be positioned and used by a user remotely from the location of the framework 20 enclosure part of the device. For example, the framework enclosure portion 20 of the device may be positioned in a location that is out of reach of the user or perhaps within an air duct of a building, bus, train, boat or other HVAC system in a building, temporary structure or transportation vehicle. When out of the reach of a user, control unit may be remotely located or incorporated into a structure or vehicle so that a user can control the workings of the equipment 10.

In various embodiments, the application of the plasma can be set to be performed for predetermined periods of time and/or at two different speeds selected with a control button 110.

In various embodiments, the portability of the equipment 10 facilitates the maneuverability and positioning thereof directly on the interior of the vehicle where it takes place or in the inlet region where air is conducted or directed into the air conditioning system of the vehicle.

Using a similar, yet different configuration, other embodiments provide a more compact sanitizing equipment device. Other embodiments may provide a sanitizing device configured into two modules that can be located or positioned remotely from one another while being incorporated into the design of the vehicle. The compacting of the equipment into two modules makes integration onboard automobiles and other means of transportation easily achievable. By virtue of a more compact design, it is possible to perform the installation and of the UVX lamp module by incorporating and/or installing it at a strategic point along or directly in the path traveled by the air used in the HVAC or air-conditioning system of the vehicle.

The tables below show tests that corroborate the efficacy of an equipment embodiment when employed in a passenger vehicle in terms of the concentration of fungi and bacteria, and the measurement of direct readings for temperature, humidity, volatile organic compounds, carbon monoxide, particulate matter and formaldehydes. The tests were conducted on two vehicles—one with the equipment and one without it.

TABLE 1

Fungi Tests
Environmental monitoring and control of possible colonization, multiplication and dissemination of fungi in the interior ambient air.

| Characterization of sampling (sampling plan) | Sample no. Recommended rates | Ambient air (CFU/$m^3$) ≤750 | Outside air (CFU/$m^3$) 0 | I/E ratio Ambient air/air (limit ≤1.5) | Genera of fungi isolated |
|---|---|---|---|---|---|
| Golf PXX1444 - with treatment | 31484/12 | 17 | 1734 | 0.0 | *Cladosporium* sp.; *Penicillium* sp.; *Rhodotorula* sp.; *Phoma* sp.; *Alternaria* sp. |

TABLE 1-continued

Fungi Tests
Environmental monitoring and control of possible colonization, multiplication and dissemination of fungi in the interior ambient air.

| Characterization of sampling (sampling plan) | Sample no. Recommended rates | Ambient air $(CFU/m^3)$ $\leq 750$ | Outside air $(CFU/m^3)$ 0 | I/E ratio Ambient air/air (limit $\leq 1.5$) | Genera of fungi isolated |
|---|---|---|---|---|---|
| Fiesta DAI4309 - without treatment | 31485/12 | 34 | 1734 | 0.0 | *Cladosporium* sp.; *Penicillium* sp.; *Rhodotorula* sp. |

Note 1:
The tests above were performed in accordance with the requirements of Resolution - RE no. 09 of MS/ANVISA of 16 Jan. 2003.

TABLE 2

Test for Bacteria
Environmental monitoring and control of possible colonization, multiplication and dissemination of bacteria in the interior ambient air.

| Characterization of sampling (sampling plan) | Sample no. Recommended rates | Ambient air $(CFU/m^3)$ $\leq 750$ | Outside air $(CFU/m^3)$ 0 | I/E ratio Ambient air/air (limit $\leq 1.5$) |
|---|---|---|---|---|
| Golf PXX1444 - with treatment | 31482/12 | 315 | 331 | 1.0 |
| Fiesta DAI4309 - without treatment | 31483/12 | 772 | 331 | 2.3 |

TABLE 3

Evaluation of temperature, humidity, volatile organic compounds, carbon monoxide, particulate matter and formaldehydes.

| Site | Temperature ° C. | Humidity (%) | VOCs $g/m^3$ | Carbon monoxide (ppm) | Aerosols $\mu g/m^3$ | Formaldehydes Ppm |
|---|---|---|---|---|---|---|
| Recommended rates | 0 | 0 | 500.0 | See note 3 | 50 | 2 [cropped] |
| Outside air | 29.5 | 41.9 | 835.7 | 3.9 | 77.3 | < [cropped] |
| Golf PXX1444 - with treatment | 22.6 | 52.4 | 432.8 | 0.5 | 6.3 | < [cropped] |
| Fiesta DAI4309 - without treatment | 24.1 | 52.1 | 624.7 | 1.3 | 62.5 | 50 [cropped] |

Note 2:
The tests above were performed in accordance with the requirements of the Green Building Council, IEQ Credit 3.2

Note 3:
According to Green Building Council, IEQ Credit 3.2, the recommended rate must be 9 ppm and not more than 2 ppm greater than the outside concentration.

Based on the above tables, equipment embodiments employed in a passenger vehicle unexpectedly decreased the amounts of volatile organic compounds, carbon monoxide, and particulate matter by significant amounts while the passenger vehicle was parked, yet running with the windows closed when compared to another similar passenger vehicle without the equipment installed. In particular, equipment embodiments decreased fungi by about 50%; decreased bacteria by about 59%; decreased VOCs by about 30%; decreased carbon monoxide by about 61%; and decreased aerosols by about 89% within the test passenger vehicle as compared to a similar passenger vehicle operating without the aid of an equipment embodiment.

Figure 1:
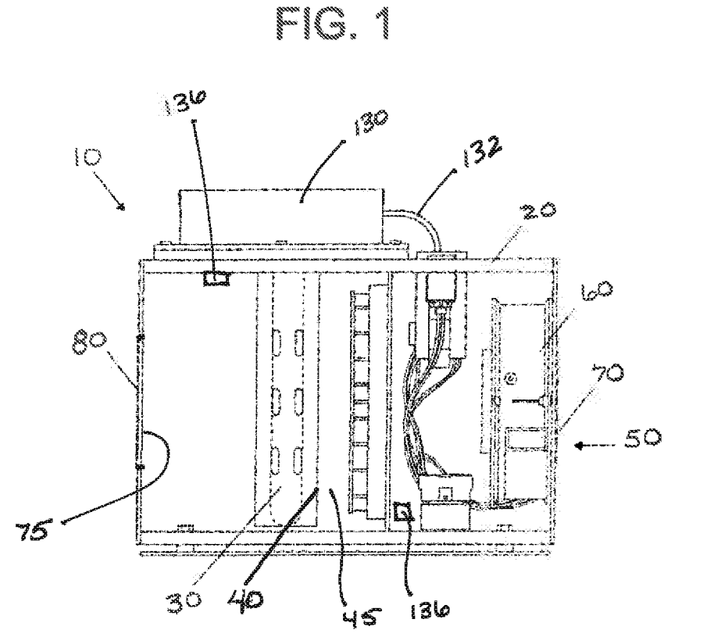
FIG. 1 is a schematic view showing main components of an embodiment of equipment for sanitizing the air conditioning system of transportation vehicles by means of radiant catalytic ionization.
Figure 2:
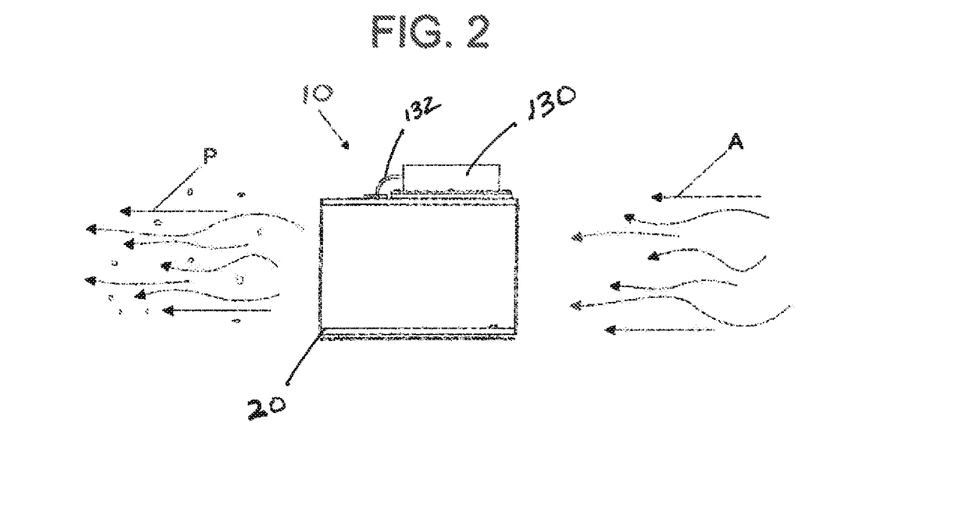
FIG. 2 is a functional schematic representation of an embodiment of the equipment for sanitizing the air conditioning system of vehicles by means of radiant catalytic ionization.
Figure 3:
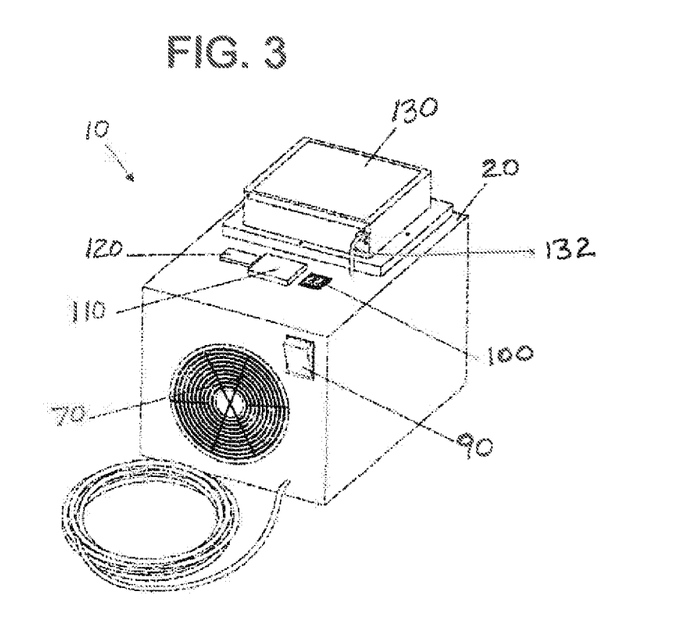
FIG. 3 is a perspective view of an embodiment of the equipment for sanitizing the air conditioning system of vehicles by means of radiant catalytic ionization.
Figure 4:
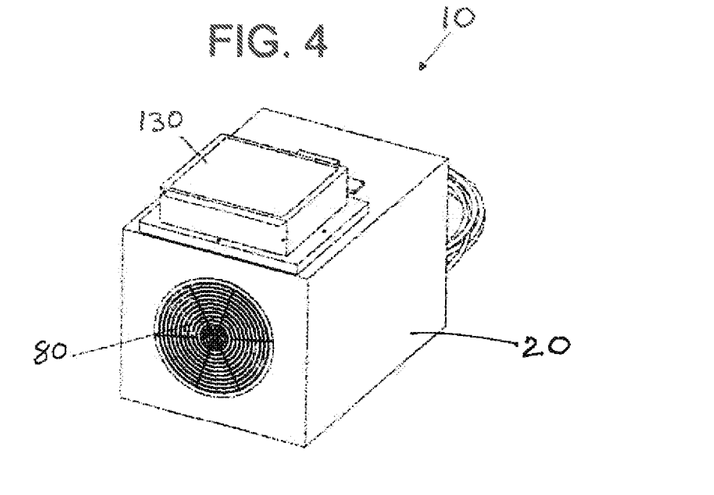
FIG. 4 is an inverted perspective view of an embodiment of the equipment for sanitizing the air conditioning system of vehicles by means of radiant catalytic ionization.
Figure 5:
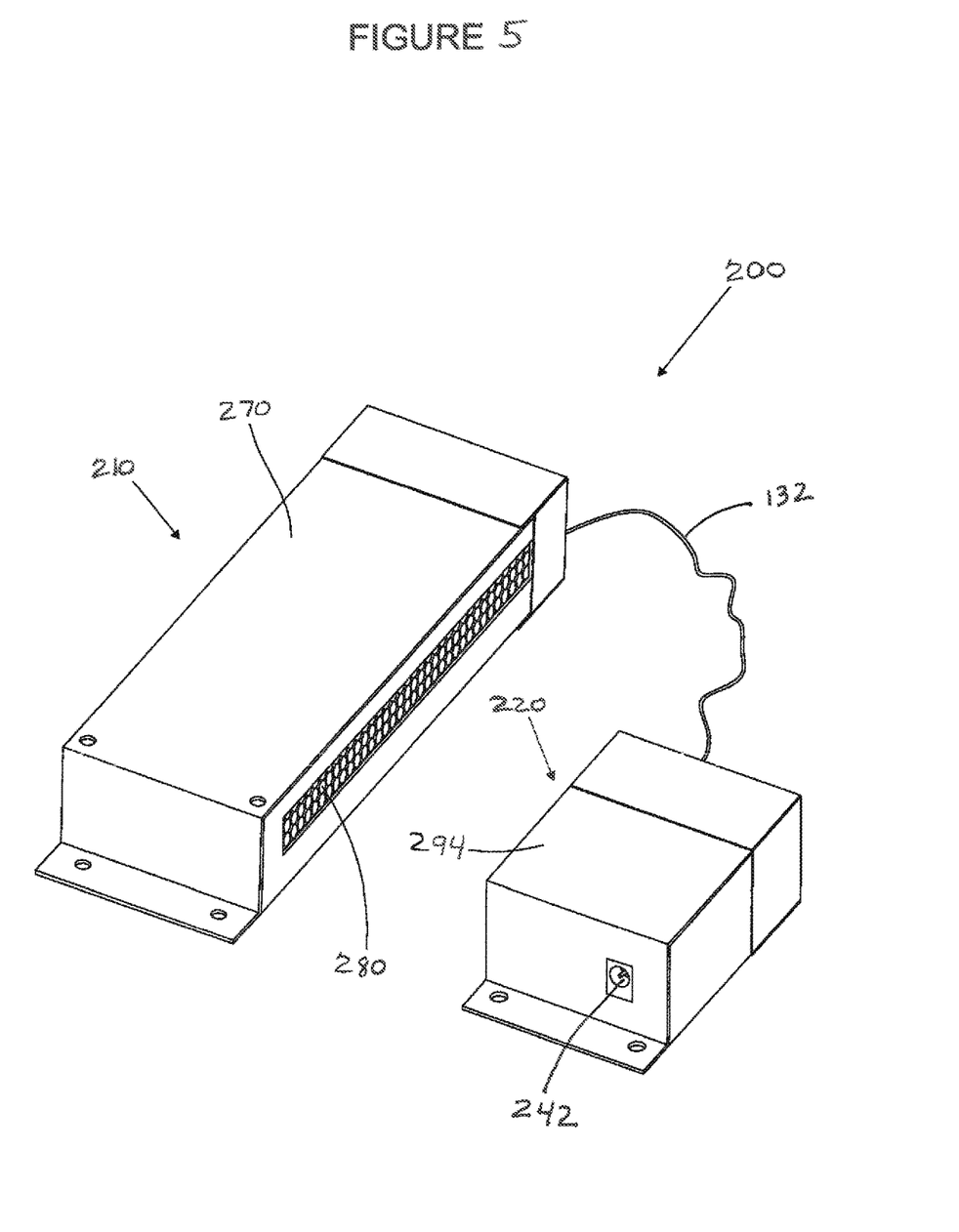
FIG. 5 is a schematic perspective view of another embodiment of the equipment for sanitizing the air conditioning system of vehicles by means of radiant catalytic ionization.
Figure 6:
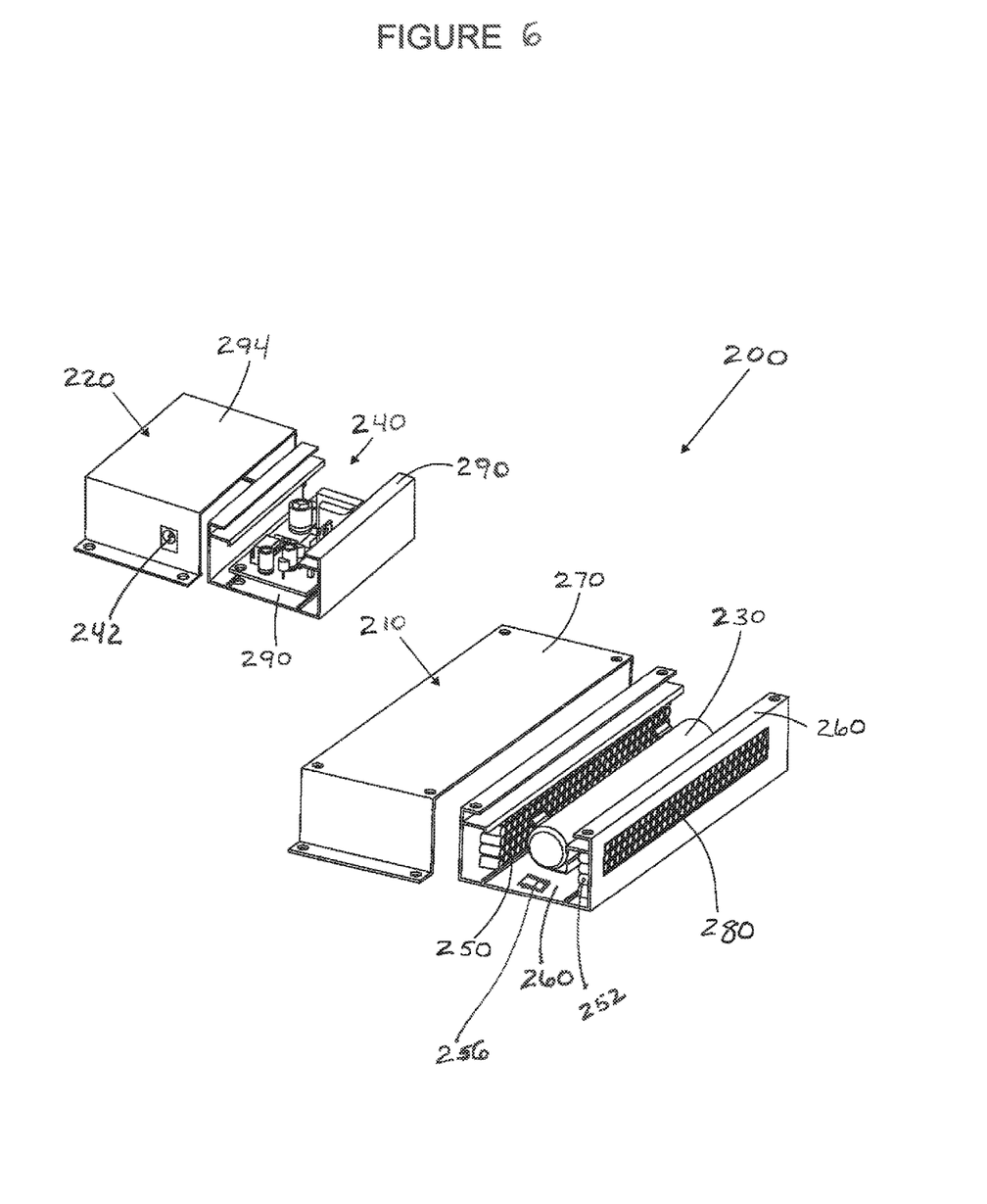
FIG. 6 is an exploded schematic perspective view of an embodiment of the equipment for sanitizing the air conditioning system of vehicles by means of radiant catalytic ionization.
Figure 7:
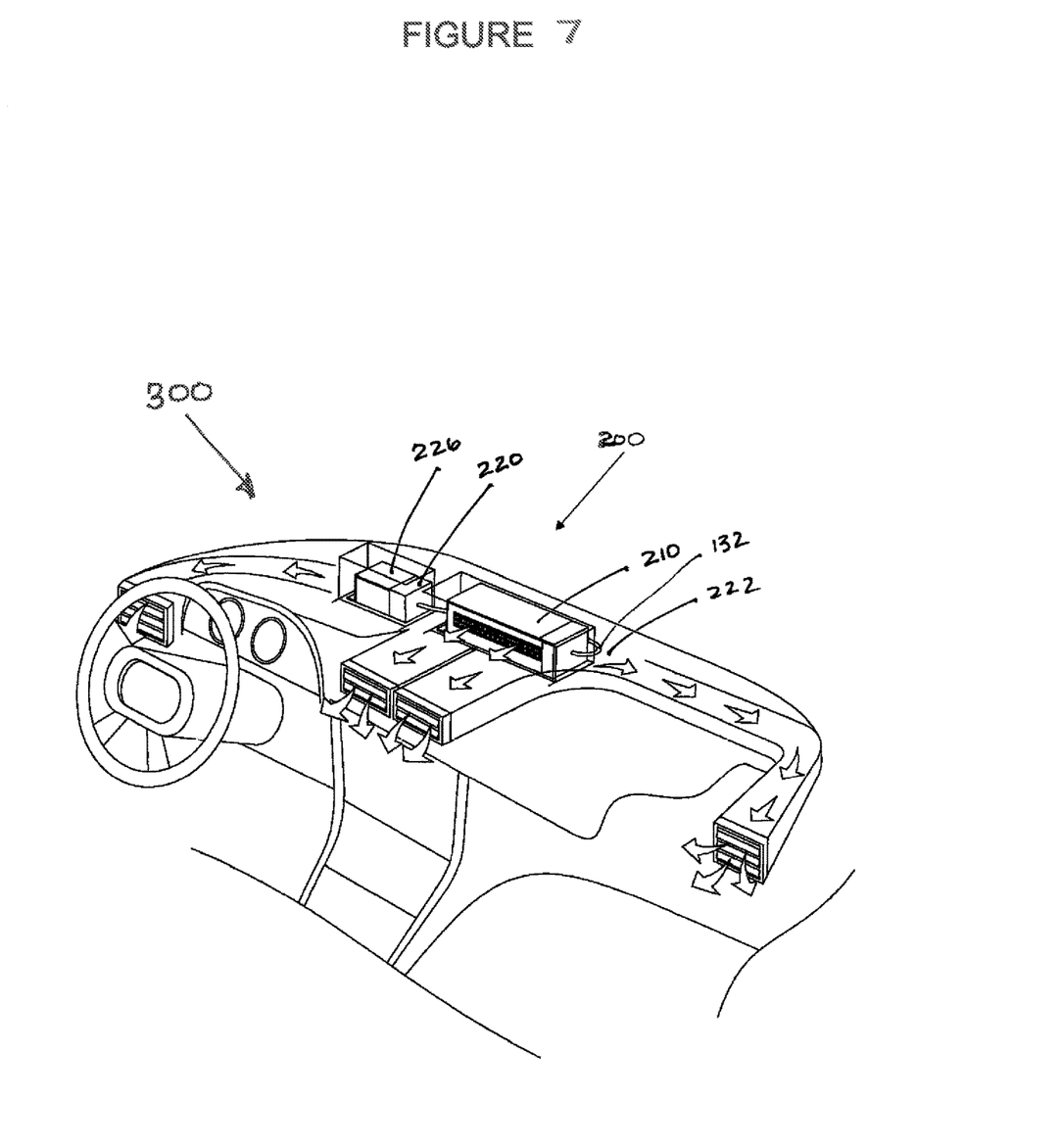
FIG. 7 is a schematic perspective view of the an embodiment of the equipment for sanitizing the air conditioning system of vehicles by means of radiant catalytic ionization showing a use condition.

Referring now to FIGS. 5, 6 and 7, another embodiment of equipment for sanitizing the air conditioning system of vehicles by means of radiant catalytic ionization 200 is shown. This embodiment of equipment 200 may be a result of decreasing the equipment overall size and separating it into two distinct modules 210 and 220. The scale of the two modules 210 and 220 is small enough so as to enable installation of the modules directly in or integrated into an air conditioning or HVAC system of transportation vehicles, such as passenger vehicles or other means of transportation including trucks, busses, trains, airplanes, construction or agriculture vehicles, boats, recreation vehicles, or other vehicles.

More particularly, the equipment 200 of this compact design may be manufactured such that a first module 210 contains the UVX lamp 230, and a second module 220 that includes a cell or control unit having respective components responsible for the powering and/or controlling the functions of the lamp 230. The first and second modules 210, 220 are preferably distinct and can be remotely located from each other so as to enable installation of the first module 210 with the UVX lamp 230 at a strategic point within or along the path traveled by air within a duct 222 used in the air-conditioning or HVAC system of the vehicle 300. Thus, air moving within a duct 222 also passes by the UVX lamp 230 and through an air permeable structure 250, shown as a honeycomb structure, and over its surfaces, which are impregnated or coated with a noble metal alloy. In some embodiments, the air moving within the duct 222 passes by the UVX lamp or bulb 230 and through an air permeable structure 250, which may be a screen, a lattice, a woven mesh, an organization of tubes or honeycomb shapes or other are permeable structure having some all of its surfaces coated or impregnated with a noble metal alloy that predominately includes titanium dioxide. The air permeable structure 250 may be positioned adjacent to and/or about a portion of the UVX lamp 230. The air coming from the forced ventilation of the vehicle, which passes through the first module 210, is subjected to a radiant catalytic ionization reaction, generating purifying plasma having a high level of sanitizing power. The purifying plasma can sanitize the air conditioning system air and duct inner surfaces. Additionally, it has been determined that the purifying plasma may also sanitize the air and the inner surfaces of the entire vehicle compartment.

In some embodiments, the first module 210 comprises a frame 260 with a covering 270 that are combined or attached to each other to form and establish an interior enclosure. Lateral openings 280 are located on opposing sides of the interior enclosure formed by the frame and covering. The lateral openings 280 allow for the passage of air moving within the air duct to go through the first air permeable structure 250 into the interior enclosure past the UVX lamp 230 and out of the interior enclosure via a second air permeable structure 252 and back into the air duct 222. In some embodiments one or more sensors 256 may be installed within the interior enclosure of the first module 210. The one or more sensors may sense humidity, temperature, or estimate the airflow movement within the first module.

In other embodiments, the first module 210 has a UVX lamp that when turned ON produces UV light. On one longitudinal side of the UVX lamp is the first air permeable structure 250. On another longitudinal side of the UVX lamp is a second air permeable structure 252. Both the first and second air permeable structures 250, 252 are impregnated or coated with a noble metal alloy that is predominantly titanium dioxide. The noble metal alloy is configured to generate by way of a radiant catalytic ionization reaction with UV light, when emitted from the UVX lamp 230, and the air proximate thereto, a purifying plasma that includes oxidative sanitizing molecules. Such oxidative sanitizing molecules include hydroxyl radicals and hydrogen peroxide. In other embodiments, a single air penetrable structure 250 is mounted to the frame 260 such that it is about a portion of or adjacent to the UVX lamp 230 and such that air moving through the duct penetrates through the air permeable structure 250.

A frame portion 260 and cover portion 270 may establish an exterior covering about the first module 210 and contain the UVX lamp 230 and the first and second air permeable structures 250, 252. The UVX lamp and first and second air permeable structures 250, 252 may be mounted on the frame portion 260 within an interior enclosure established by the frame and, in some embodiments, the cover portion 270. Cut-away portions or lateral openings 280 enable lateral passage of air into and out of the interior of the first module 210 by way of passing through the first and second air permeable structure 250, 252 when the first module is positioned within an air duct or integrated into an air duct structure of an HVAC system of a transportation vehicle.

Additionally, embodiments may include a second module 220 located remotely from the first module and within the transportation vehicle. The second module 220 may be electrically connected to the first module 210. The second module 220 includes a cell or control circuitry 240 that provides power and controls the functions of the UVX lamp 230 within the first module 210. The control circuitry 240 may also be configured to be connected 242 to other circuitry within the transportation vehicle 300. The cell or control circuitry 240 may be attached to a frame portion 290 of the second module 220. A cover portion 294 may combine and attach to the frame portion 290 to establish an exterior covering of the second module such that the control circuitry is enclosed within the covering.

As shown in FIG. 7, the second module 220 may be positioned remotely from the first module 210. An electrical connection is provided between the first and second modules to enable the second module to provide power and to share control signals to and from the first module in order to control and monitor the workings of the UVX bulb and other sensors 256, such as humidity, temperature (air, bulb or honeycomb structure) and the air flow rate through the first module. The control circuitry 240 may comprise a ballast or other voltage and current controlling circuitry so as to enable the control circuitry 240 to provide appropriate voltage and current to the UVX lamp or bulb 230. The control circuitry 240 may use the sensed output from the sensors for a variety of purposes. For example, it has been found that the amount of humidity in the HVAC air affects the rate of radiant catalytic ionization reaction that occurs to create the purifying plasma. As such, if the humidity sensor indicates that the humidity is below a predetermined low humidity indication, the control circuitry may turn the UVX bulb OFF. Conversely, if the humidity sensor indicates that the humidity is above a predetermined high humidity indication, the control circuitry may lower the power to or intensity of UV light emitted by the of the UVX bulb in order to save energy, increase the life expectancy of the UVX bulb, or decrease the efficiency of the radiant catalytic ionization reaction. With respect to the temperature sensor, this sensor may be used to sense the temperature of the air and plasma output by the first module. The control circuitry may compare this output temperature with other signals or data and determine whether to turn OFF the UVX bulb. For example, if the HVAC system of the vehicle is set to high so as to cool the interior of the vehicle quickly to a predetermined cooler temperature set by a vehicle occupant, it may be advantageous to turn OFF the UVX bulb until there is an indication received by the control circuit 240 from other vehicle control circuitry 226 indicating that the interior of the vehicle is within about 2 to 10 degrees Fahrenheit of being at the predetermined cooler temperature set the vehicle occupant.

With respect to the air flow rate sensor, this sensor may provide feedback to the control circuit 240 so that the power to the UVX bulb 230 is increased or decreased in order to produce more or less UV output depending of the estimated flow rate of the air through the first module 210. Additionally, if the flow rate sensor determines that the flow rate is below predetermined flow rate (perhaps due to a fan malfunction in the HVAC system, or if a temperature sensor senses that the temperature in or about the first module is above a predetermined safe maximum temperature, the control circuitry may turn the UVX bulb OFF.

In additional embodiments, the UVX bulb 230 may be comprised of a plurality of UVX light emitting diodes (LEDs) positioned within the first module so as to illuminate the surfaces of the air permeable structures 250, 252 in order to generate the purifying plasma via radiant catalytic ionization.

In this context, when the air conditioning or HVAC system is switched ON, the UVX lamp 230 is lit, thus bringing about the transformation of air passing through or about the first module 210 into purifying plasma composed of hydroxyl radicals and hydrogen peroxide. The purifying plasma can be applied according to the ventilation speeds of the air conditioning system of automobiles, and its respective resources, depending on the vehicle.

Moreover, the equipment 200 can also be applied or installed to be a component of air conditioning or HVAC systems of other land, sea or air vehicles such as, for example, trains, subways, boats, airplanes, or construction or agricultural vehicles.

It will be appreciated by those skilled in the art having the benefit of this disclosure that this equipment for sanitizing the air conditioning system of vehicles by means of radiant catalytic ionization provides a system and device that can be incorporated into or used in conjunction with a HVAC system to significantly reduce the concentration of fungi, bacteria, volatile organic compounds (VOCs) carbon monoxide, and particulate matter and in effect clean the ducts, air and interior surfaces of a vehicle. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A device comprising:
    a first module comprising:
        a UVX lamp configured to produce UV light;
        a first and a second honeycomb structure of surfaces, each honeycomb structure having surfaces impregnated or coated with a noble metal alloy and configured to generate, via a radiant catalytic ionization reaction with the UV light, a purifying plasma comprising oxidative sanitizing molecules; the first and second honeycomb structures each being positioned adjacent to the UVX lamp such that the UV light can impinge on a majority of the surfaces while air flows there over;
        a first frame on which the UVX lamp, the first and the second honeycomb structures of surfaces are mounted; and
        a first cover portion that combines with the first frame to establish an enclosure that enables passage of air through the first and second honeycomb structures and surfaces when the first module is positioned in a duct of a HVAC system of a transportation vehicle; and
    a second module located remotely from the first module, the second module being connected to the first module by an electrical connection, the second module comprising:
        control circuitry that includes components that power and control functions of the UVX lamp and connections to control circuitry of the transportation vehicle, the second module being configured to be positioned within or proximate to a control console of the transportation vehicle while being remote from the first module.

2. The device of claim 1, wherein the first module further comprises a fan for pushing or pulling air to flow over the surfaces of the first and second honeycomb structures.

3. The device of claim 1, wherein the first cover portion is integral with the duct of the HVAC system.

4. The device of claim 1, wherein the UVX lamp comprises a plurality of UVX LEDs.

5. The device of claim 1, wherein the purifying plasma further comprises hydrogen peroxide and hydroxyl radicals.

6. The device of claim 1, wherein the duct of the HVAC system is an output duct that passes HVAC system treated air into a passenger compartment of the transportation vehicle.

7. The device of claim 1, wherein the first cover portion combines with the first frame to establish an exterior covering about the first module with openings that enable air to pass through the first and second honeycomb structure surfaces.

8. The device of claim 1, further comprising a temperature sensor configured to sense an output temperature of the plasma from the first module, wherein the control circuitry is configured to turn off the UVX lamp if the sensed output temperature is greater than a predetermined temperature when the HVAC system of the transportation vehicle is set to cool the interior air of the transportation vehicle to user set temperature at a maximum rate.

9. The device of claim 1, further comprising an air flow sensor configured to sense a flow of air or plasma through the first module, wherein the control circuitry is configured to turn off the UVX lamp if the sensed output of the air flow sensor indicates that the flow of air or plasma is below a predetermined flow rate.

10. A transportation vehicle comprising:
    an HVAC system, integrated into the transportation vehicle, comprising an air duct configured to distribute conditioned air into the interior of the transportation vehicle;
    an air sanitizing device integrated into the HVAC system, the air sanitizing device comprising:
    a first module comprising:
        a UVX lamp configured to produce UV light;
        a first air permeable structure having surfaces impregnated or coated with a noble metal alloy and configured to generate, via a radiant catalytic ionization reaction with the UV light, a purifying plasma comprising oxidative sanitizing molecules; the first air permeable structure being positioned adjacent to the UVX lamp such that the UV light can impinge on air permeable structure's surfaces while air flows there over;
        a first frame on which the UVX lamp and the first air permeable structure is mounted; the first frame being configured for and positioned in the air duct such that air is enabled to pass through the first air permeable structure surfaces; and a second module located remotely from the first module, the second module being connected to the first module by an electrical connection, the second module comprising:

control circuitry that includes components that power and control functions of the UVX lamp and connections to control circuitry of the transportation vehicle, the second module being configured to be positioned within or proximate to a control console of the transportation vehicle while being remote from the first module.

11. The transportation vehicle of claim 10, wherein the first module further comprises a first cover portion that combines with the first frame to establish an enclosure that enables passage of air through the first air permeable structure.

12. The transportation vehicle of claim 11, wherein the first cover portion is integral with the air duct of the HVAC system.

13. The transportation vehicle of claim 11, wherein the UVX lamp comprises a plurality of UVX LEDs.

14. The device of claim 10, wherein the noble metal alloy comprises titanium dioxide and wherein the purifying plasma further comprises hydrogen peroxide and hydroxyl radicals.

15. An air sanitizing device configured to be integrated with an HVAC system of a transportation vehicle, the air sanitizing device comprising:

a first module comprising:
a UVX lamp configured to produce UV light;
an air permeable structure having surfaces impregnated or coated with a noble metal alloy and configured to generate, via a radiant catalytic ionization reaction with the UV light, a purifying plasma comprising oxidative sanitizing molecules; the air permeable structure being positioned adjacent to the UVX lamp such that the UV light can impinge on a majority of the surfaces while air flows there over;

a first frame on which the UVX lamp and the air permeable structure are mounted; the first frame being configured to be positioned in the air duct such that air is enabled to pass through and about the air permeable structure and over the surfaces; and a second module located remotely from the first module, the second module being connected to the first module by an electrical connection, the second module comprising:

control circuitry that includes components that power and control functions of the UVX lamp and connections to control circuitry of the transportation vehicle, the second module being configured to be positioned within or proximate to a control console of the transportation vehicle while being remote from the first module.

16. The air sanitizing device of claim 15, wherein the first module further comprises a first cover portion that combines with the first frame to establish an enclosure that enables passage of air through the first and second honeycomb structure surfaces.

17. The air sanitizing device of claim 15, wherein the first cover portion is integral with the air duct of the HVAC system.

18. The air sanitizing device of claim 15, wherein the UVX lamp comprises a plurality of UVX LEDs.

19. The air sanitizing device of claim 15, wherein the purifying plasma further comprises hydrogen peroxide and hydroxyl radicals.

20. The air sanitizing device of claim 15, wherein the first module is mounted to extend into an interior of the air duct of the HVAC system inside the transportation vehicle, and wherein the transportation vehicle is an automobile.

* * * * *